(12) United States Patent
Pimenta et al.

(10) Patent No.: US 9,186,261 B2
(45) Date of Patent: Nov. 17, 2015

(54) SYSTEM AND METHODS FOR SPINAL FUSION

(71) Applicant: NuVasive, Inc., San Diego, CA (US)

(72) Inventors: Luiz Pimenta, Sao Paula (BR); Jared Arambula, San Diego, CA (US); Benjamin VerHage, New York, NY (US); Troy Woolley, Erie, CO (US); Patrick Miles, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 76 days.

(21) Appl. No.: 14/193,886

(22) Filed: Feb. 28, 2014

(65) Prior Publication Data

US 2014/0180423 A1    Jun. 26, 2014

Related U.S. Application Data

(63) Continuation of application No. 12/044,917, filed on Mar. 7, 2008, now Pat. No. 8,673,005.

(60) Provisional application No. 60/905,674, filed on Mar. 7, 2007.

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/447* (2013.01); *A61F 2/4611* (2013.01); *A61F 2002/2817* (2013.01); *A61F 2002/2835* (2013.01); *A61F 2002/3008* (2013.01); *A61F 2002/30082* (2013.01); *A61F 2002/30266* (2013.01); *A61F 2002/30774* (2013.01);
(Continued)

(58) Field of Classification Search
CPC ...... A61F 2/4455; A61F 2/446; A61F 2/4465; A61F 2/447; A61F 2/4611; A61F 2002/30841; A61F 2002/30904; A61F 2002/4475; A61F 2002/3008; A61F 2002/30266
USPC ........................................... 623/17, 11, 17.16
See application file for complete search history.

(56) References Cited

U.S. PATENT DOCUMENTS 3,486,505 A    12/1969    Morrison
3,518,993 A    7/1970     Blake
(Continued)

FOREIGN PATENT DOCUMENTS

CA    2015507    1/1999
EP    369603     5/1990
(Continued)

OTHER PUBLICATIONS

Alleyne, Cargill, H., et al., "Current and future approaches to lumbar disc surgery: A literature review", *Medscape Orthopedics & Sports Medicine*, 1, [www.medscape.com/Medscape/OrthoSportsMed/1997/v01.nll/.../mos3057], (1997).
(Continued)

*Primary Examiner* — Jerry Cumberledge
*Assistant Examiner* — Nicholas Plionis
(74) *Attorney, Agent, or Firm* — Fish & Richardson P.C.

(57) ABSTRACT

A spinal fusion system and related methods involve the use of a spinal fusion implant of non-bone construction. The spinal fusion implant is particularly suited for introduction into the disc space via a lateral approach to the spine.

20 Claims, 7 Drawing Sheets

(51) Int. Cl.
*A61F 2/28* (2006.01)
*A61F 2/30* (2006.01)

(52) U.S. Cl.
CPC .......... *A61F 2002/30777* (2013.01); *A61F 2002/30785* (2013.01); *A61F 2002/30841* (2013.01); *A61F 2002/30904* (2013.01); *A61F 2002/4475* (2013.01); *A61F 2002/4623* (2013.01); *A61F 2002/4627* (2013.01); *A61F 2002/4629* (2013.01)

(56) References Cited

U.S. PATENT DOCUMENTS

| | | |
|---|---|---|
| 3,604,487 A | 9/1971 | Gilbert |
| 3,745,995 A | 7/1973 | Kraus |
| 3,848,601 A | 11/1974 | Ma et al. |
| 3,867,728 A | 2/1975 | Stubstad et al. |
| 4,026,304 A | 5/1977 | Levy |
| 4,026,305 A | 5/1977 | Brownlee et al. |
| 4,349,921 A | 9/1982 | Kuntz |
| 4,454,374 A | 6/1984 | Pollack |
| 4,501,269 A | 2/1985 | Bagby |
| 4,545,374 A | 10/1985 | Jacobson |
| 4,646,738 A | 3/1987 | Trott |
| 4,657,550 A | 4/1987 | Daher |
| 4,743,256 A | 5/1988 | Brantigan |
| 4,781,591 A | 11/1988 | Allen |
| 4,834,757 A | 5/1989 | Brantigan |
| 4,877,020 A | 10/1989 | Vich |
| 4,878,915 A | 11/1989 | Brantigan |
| 4,932,975 A | 6/1990 | Main et al. |
| 4,950,296 A | 8/1990 | McIntyre |
| 4,961,740 A | 10/1990 | Ray et al. |
| 4,962,766 A | 10/1990 | Herzon |
| 5,015,247 A | 5/1991 | Michelson |
| 5,026,373 A | 6/1991 | Ray et al. |
| 5,047,055 A | 9/1991 | Bao et al. |
| 5,055,104 A | 10/1991 | Ray |
| 5,062,845 A | 11/1991 | Kuslich et al. |
| 5,071,437 A | 12/1991 | Steffee |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharodi |
| 5,192,327 A | 3/1993 | Brantigan |
| 5,217,497 A | 6/1993 | Mehdian |
| 5,263,953 A | 11/1993 | Bagby |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,397,364 A | 3/1995 | Kozak |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,484,403 A | 1/1996 | Yoakum et al. |
| 5,484,437 A | 1/1996 | Michelson |
| 5,489,307 A | 2/1996 | Kuslich et al. |
| 5,489,308 A | 2/1996 | Kuslich et al. |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,688 A | 7/1996 | Navas |
| 5,545,222 A | 8/1996 | Bonutti |
| 5,545,688 A | 8/1996 | Huang |
| 5,562,736 A | 10/1996 | Ray et al. |
| 5,565,005 A | 10/1996 | Erickson et al. |
| 5,571,190 A | 11/1996 | Ulrich |
| 5,571,192 A | 11/1996 | Schonhoffer |
| 5,593,409 A | 1/1997 | Michelson |
| 5,607,424 A | 3/1997 | Tropiano |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,596 A | 7/1997 | Kim et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A | 11/1997 | Rinner |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zuckerman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar et al. |
| 5,703,451 A | 12/1997 | Yamamichi et al. |
| 5,707,373 A | 1/1998 | Sevrain et al. |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,779,642 A | 7/1998 | Nightengale |
| 5,782,830 A | 7/1998 | Farris |
| 5,782,919 A | 7/1998 | Zdeblick et al. |
| 5,785,710 A | 7/1998 | Michelson |
| 5,797,909 A | 8/1998 | Michelson |
| 5,800,549 A | 9/1998 | Bao et al. |
| 5,800,550 A | 9/1998 | Sertich |
| 5,814,084 A | 9/1998 | Grivas et al. |
| 5,814,550 A | 9/1998 | Wolcott |
| 5,851,084 A | 12/1998 | Nishikawa |
| 5,851,208 A | 12/1998 | Trott |
| 5,860,973 A | 1/1999 | Michelson |
| 5,865,845 A | 2/1999 | Thalgott |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,890 A | 4/1999 | Pisharodi |
| 5,904,719 A | 5/1999 | Errico et al. |
| 5,910,315 A | 6/1999 | Stevenson et al. |
| 5,942,698 A | 8/1999 | Stevens |
| 5,954,769 A | 9/1999 | Rosenlicht |
| 5,968,098 A | 10/1999 | Winslow |
| 5,993,474 A | 11/1999 | Ouchi |
| 6,003,426 A | 12/1999 | Kobayashi et al. |

(56) References Cited

U.S. PATENT DOCUMENTS

| | | |
|---|---|---|
| 6,004,326 A | 12/1999 | Castro et al. |
| 6,008,433 A | 12/1999 | Stone |
| 6,015,436 A | 1/2000 | Schunhuffer |
| 6,033,405 A | 3/2000 | Winslow et al. |
| 6,033,438 A | 3/2000 | Bianchi et al. |
| 6,039,761 A | 3/2000 | Li et al. |
| 6,042,582 A | 3/2000 | Ray |
| 6,045,580 A | 4/2000 | Scarborough et al. |
| 6,045,582 A | 4/2000 | Prybyla |
| 6,048,342 A | 4/2000 | Zucherman et al. |
| 6,059,829 A | 5/2000 | Schlapfer et al. |
| 6,063,088 A | 5/2000 | Winslow |
| 6,080,155 A | 6/2000 | Michelson |
| 6,083,225 A | 7/2000 | Winslow et al. |
| 6,096,080 A | 8/2000 | Nicholson et al. |
| 6,102,948 A | 8/2000 | Brosnahan, III |
| 6,120,503 A | 9/2000 | Michelson |
| 6,120,506 A | 9/2000 | Kohrs et al. |
| 6,132,472 A | 10/2000 | Bonutti |
| 6,143,033 A | 11/2000 | Paul et al. |
| 6,159,211 A | 12/2000 | Boriani et al. |
| 6,159,215 A | 12/2000 | Urbahns et al. |
| 6,193,756 B1 | 2/2001 | Studer et al. |
| 6,200,347 B1 | 3/2001 | Anderson |
| 6,224,607 B1 | 5/2001 | Michelson |
| 6,224,631 B1 | 5/2001 | Kohrs |
| 6,241,769 B1 | 6/2001 | Nicholson et al. |
| 6,241,770 B1 | 6/2001 | Michelson |
| 6,241,771 B1 | 6/2001 | Gresser et al. |
| 6,251,140 B1 | 6/2001 | Marino et al. |
| 6,258,125 B1 | 7/2001 | Paul et al. |
| 6,277,149 B1 | 8/2001 | Boyle et al. |
| 6,304,487 B1 | 10/2001 | Pawletko et al. |
| 6,319,257 B1 | 11/2001 | Carignan et al. |
| 6,371,989 B1 | 4/2002 | Chauvin et al. |
| 6,383,221 B1 | 5/2002 | Scarborough et al. |
| 6,409,766 B1 | 6/2002 | Brett |
| 6,425,772 B1 | 7/2002 | Bernier et al. |
| 6,426,772 B1 | 7/2002 | Yoneyama et al. |
| 6,432,140 B1 | 8/2002 | Lin |
| 6,440,142 B1 | 8/2002 | Ralph et al. |
| 6,442,814 B1 | 9/2002 | Landry et al. |
| 6,447,547 B1 | 9/2002 | Michelson |
| 6,454,806 B1 | 9/2002 | Cohen et al. |
| 6,468,311 B2 | 10/2002 | Boyd et al. |
| 6,491,724 B1 | 12/2002 | Ferree |
| 6,527,773 B1 | 3/2003 | Lin et al. |
| D472,634 S | 4/2003 | Anderson |
| D473,650 S | 4/2003 | Anderson |
| 6,547,823 B2 | 4/2003 | Scarborough et al. |
| 6,562,072 B1 | 5/2003 | Fuss et al. |
| 6,595,998 B2 | 7/2003 | Johnson et al. |
| 6,599,294 B2 | 7/2003 | Fuss et al. |
| 6,626,905 B1 | 9/2003 | Schmiel et al. |
| 6,635,086 B2 | 10/2003 | Lin |
| 6,648,895 B2 | 11/2003 | Burkus et al. |
| 6,672,019 B1 | 1/2004 | Wenz |
| 6,676,703 B2 | 1/2004 | Biscup |
| 6,706,067 B2 | 3/2004 | Shimp et al. |
| 6,723,097 B2 | 4/2004 | Fraser et al. |
| 6,743,255 B2 | 6/2004 | Ferree |
| 6,746,484 B1 | 6/2004 | Liu et al. |
| 6,755,841 B2 | 6/2004 | Fraser et al. |
| 6,761,739 B2 | 7/2004 | Shepard |
| 6,824,564 B2 | 11/2004 | Crozet |
| 6,830,570 B1 | 12/2004 | Frey et al. |
| D503,801 S | 4/2005 | Jackson |
| 6,923,814 B1 | 8/2005 | Hildebrand et al. |
| 6,942,698 B1 | 9/2005 | Jackson |
| 6,964,687 B1 | 11/2005 | Bernard et al. |
| 6,974,480 B2 | 12/2005 | Messerli et al. |
| 6,979,353 B2 | 12/2005 | Bresina |
| 6,984,245 B2 | 1/2006 | McGahan et al. |
| 6,986,788 B2 | 1/2006 | Paul et al. |
| 6,989,031 B2 | 1/2006 | Michelson |
| 7,018,416 B2 | 3/2006 | Hanson et al. |
| D530,423 S | 10/2006 | Miles et al. |
| 7,125,425 B2 | 10/2006 | Foley et al. |
| 7,192,447 B2 | 3/2007 | Rhoda |
| 7,244,258 B2 | 7/2007 | Burkus et al. |
| 7,303,583 B1 | 12/2007 | Schaer et al. |
| 7,326,251 B2 | 2/2008 | McCombe et al. |
| 7,867,277 B1 | 1/2011 | Tohmeh |
| 7,951,203 B2 | 5/2011 | McCombe et al. |
| 8,021,430 B2 | 9/2011 | Michelson |
| 8,187,334 B2 | 5/2012 | Curran et al. |
| 8,246,686 B1 | 8/2012 | Curran et al. |
| 8,251,997 B2 | 8/2012 | Michelson |
| 8,361,156 B2 | 1/2013 | Curran et al. |
| 8,425,612 B2 | 4/2013 | Perez-Cruet et al. |
| 8,506,630 B2 | 8/2013 | Wardlaw |
| 8,506,636 B2 | 8/2013 | Dye |
| 8,574,301 B2 | 11/2013 | Curran et al. |
| 8,579,909 B2 | 11/2013 | Burkus et al. |
| 8,591,589 B2 | 11/2013 | McCombe et al. |
| 8,608,804 B2 | 12/2013 | Curran et al. |
| 2001/0016741 A1 | 8/2001 | Burkus et al. |
| 2002/0019637 A1 | 2/2002 | Frey et al. |
| 2002/0058950 A1 | 5/2002 | Winterbottom et al. |
| 2002/0068936 A1 | 6/2002 | Burkus et al. |
| 2002/0116008 A1 | 8/2002 | Lin et al. |
| 2002/0165550 A1 | 11/2002 | Frey et al. |
| 2003/0023306 A1 | 1/2003 | Liu et al. |
| 2003/0028249 A1 | 2/2003 | Baccelli et al. |
| 2003/0100950 A1 | 5/2003 | Moret |
| 2003/0105528 A1 | 6/2003 | Shimp et al. |
| 2003/0139812 A1 | 7/2003 | Garcia et al. |
| 2003/0139813 A1 | 7/2003 | Messerli |
| 2003/0149438 A1 | 8/2003 | Nichols et al. |
| 2004/0024408 A1 | 2/2004 | Burkus et al. |
| 2004/0153155 A1 | 8/2004 | Chung et al. |
| 2004/0176775 A1 | 9/2004 | Burkus et al. |
| 2004/0199251 A1 | 10/2004 | McCombe et al. |
| 2005/0059971 A1 | 3/2005 | Michelson |
| 2005/0187625 A1 | 8/2005 | Wolek et al. |
| 2005/0197702 A1 | 9/2005 | Coppes et al. |
| 2005/0203538 A1 | 9/2005 | Lo et al. |
| 2006/0074488 A1 | 4/2006 | Abdou |
| 2006/0142864 A1 | 6/2006 | Cauthen |
| 2007/0179612 A1 | 8/2007 | Johnson et al. |
| 2007/0191945 A1 | 8/2007 | Yu et al. |
| 2007/0276499 A1 | 11/2007 | Paul et al. |
| 2007/0288007 A1 | 12/2007 | Burkus et al. |
| 2008/0015701 A1 | 1/2008 | Garcia et al. |
| 2008/0058838 A1 | 3/2008 | Steinberg |
| 2008/0065219 A1 | 3/2008 | Dye |
| 2008/0119937 A1 | 5/2008 | McCombe et al. |
| 2009/0222099 A1 | 9/2009 | Liu et al. |
| 2010/0106250 A1 | 4/2010 | Abdou |
| 2011/0112642 A1 | 5/2011 | Tohmeh |
| 2011/0196496 A1 | 8/2011 | McCombe et al. |
| 2012/0078374 A1 | 3/2012 | Villiers et al. |
| 2012/0158141 A1 | 6/2012 | Johnson et al. |
| 2012/0179261 A1 | 7/2012 | Soo |
| 2012/0209388 A1 | 8/2012 | Curran et al. |
| 2012/0215317 A1 | 8/2012 | Curran et al. |
| 2013/0006363 A1 | 1/2013 | Ullrich et al. |
| 2013/0138216 A1 | 5/2013 | Curran et al. |
| 2013/0144390 A1 | 6/2013 | Curran et al. |
| 2013/0245771 A1 | 9/2013 | Michelson |

FOREIGN PATENT DOCUMENTS

| | | |
|---|---|---|
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| WO | 90/00037 | 1/1990 |

(56) References Cited

FOREIGN PATENT DOCUMENTS

| | | |
|---|---|---|
| WO | 91/06261 | 5/1991 |
| WO | 92/14423 | 9/1992 |
| WO | 93/01771 | 2/1993 |
| WO | 94/04100 | 3/1994 |
| WO | 94/10928 | 5/1994 |
| WO | 95/01810 | 1/1995 |
| WO | 95/08306 | 3/1995 |
| WO | 96/08205 | 3/1996 |
| WO | 96/17564 | 3/1996 |
| WO | 96/41582 | 12/1996 |
| WO | 97/20513 | 6/1997 |
| WO | 97/33525 | 9/1997 |
| WO | 97/37620 | 10/1997 |
| WO | 98/09586 | 3/1998 |
| WO | 98/14142 | 4/1998 |
| WO | 98/17208 | 4/1998 |
| WO | 98/25539 | 6/1998 |
| WO | 99/08627 | 2/1999 |
| WO | 99/38461 | 8/1999 |
| WO | 00/44288 | 8/2000 |
| WO | 00/45712 | 8/2000 |
| WO | 00/45713 | 8/2000 |
| WO | 01/41681 | 6/2001 |
| WO | 01/49333 | 7/2001 |

OTHER PUBLICATIONS

Baulot, et al., "Complementary anterior spondylodesis by thoracoscopy. Technical note regarding an observation", *Lyon Surg.*, 90(5):347-351 (1994).
Benini, et al., "Undercutting decompression and posterior fusion with translaminar facet screw fixation in degenerative lumbar spinal stenosis: Technique and results", *Neuro-Orthopedics*, 17/18, 159-172 (1995).
Berry, et al., "A morphometric study of human lumbar and selected thoracic vertebrae, study of selected vertebrae" *Spine* 12(4):362-367 (1996).
CoRoent® XL & XLR Marketing Brochure (9004225 B.0), *NuVasive, Inc.*, 2006, 2 pages.
CoRoent® XL & XLR Marketing Brochure (9004225 C.0), *NuVasive, Inc.*, 2007, 2 pages.
CoRoent® XL Marketing Brochure (9500039 A.0), *NuVasive, Inc.*, 2006, 8 pages.
CoRoent™ Marketing Brochure (9004001 A.0), *NuVasive, Inc.*, 2004, 2 pages.
CoRoent™ Marketing Brochure (9004001 C.0), *NuVasive, Inc.*, 2005, 2 pages.
CoRoent™ XL & XLR Marketing Brochure (9004225 A.0), *NuVasive, Inc.*, 2005, 2 pages.
Counterclaim Defendants' Corrected Amended Invalidity Contentions re U.S. Pat. No. 8,000,782; 8,005,535; 8,016,767; 8,192,356; 8,187,334; 8,361,156, D652,922; D666,294 re Case No. 3:12-cv-02738-CAB(MDD), dated Aug. 19, 2013, 30 pages.
Crock, H. V., "A Short Practice of Spinal Surgery", Second, revised edition, published by Springer-Verlag/Wein, New York (1993).
Crock. H. V., "Anterior Lumbar Interbody Fusion" *Clinical Orthopaedics & Related Research*, Marshall R. Urist, Editor-in-Chief, J. B. Lippincott Company (1982).
Declaration of Mary Phelps Regarding Telamon Verte-Stack PEEK Vertebral Body Spacer, dated Aug. 13, 2013, 9 pages.
Declaration of Richard A. Hynes, M.D. Regarding U.S. Pat. No. 8,187,334, dated Aug. 14, 2013, 74 pages.
Declaration of Richard A. Hynes, M.D. Regarding U.S. Pat. No. 8,361,156, dated Aug. 14, 2013, 74 pages.
Declaration of Steven D. DeRidder regarding U.S. Patent Application Publication No. 2002/0165550, Jul. 30, 2013, 5 pages.
Edeland, H.G., "Some additional suggestions for an intervertebral disc prothesis", *Journal of Biomedical Engineering*, 7:57-62 (1985).
Kambin, et al., "History and current status of percutaneous arthroscopic disc surgery", *Spine*, 21(24S):57S-61S (1996).
Kemp, H. B. S., "Anterior fusion of the spine for infective lesions in adults", *Journal of Bone & Joint Surgery*, 55B(4):715-734 (1973).
Medtronic Sofamor Danek USA, Inc. "Boomerang I Verte-Stack PEEK Vertebral Body Brochure," 2003, 6 pages.
Medtronic Sofamor Danek USA, Inc. "Boomerang I Verte-Stack PEEK Vertebral Body Spacer Implant," Apr. 26, 2001, 8 pages.
Medtronic Sofamor Danek USA, Inc. "Boomerang II Verte-Stack PEEK Vertebral Body Spacer Brochure," 2004, 4 pages.
Medtronic Sofamor Danek USA, Inc. "Boomerang II Verte-Stack PEEK Vertebral Body Spacer Implant," Dec. 17, 2003, 9 pages.
Medtronic Sofamor Danek USA, Inc. "Boomerang Prototype Verte-Stack PEEK Vertebral Body Spacer Implant," May 7, 2000, 8 pages.
Medtronic Sofamor Danek USA, Inc. "PCR PEEK Cement Restrictor Brochure," 2001, 2 pages.
Medtronic Sofamor Danek USA, Inc. "PCR PEEK Cement Restrictor Implant," Oct. 2, 2001, 17 pages.
Medtronic Sofamor Danek USA, Inc. "Telemon Verte-Stack PEEK Vertebral Body Spacer Brochure I," 2003, 2 pages.
Medtronic Sofamor Danek USA, Inc. "Telemon Verte-Stack PEEK Vertebral Body Spacer Brochure II," 2003, 10 pages.
Medtronic Sofamor Danek USA, Inc. "Telemon Verte-Stack PEEK Vertebral Body Spacer Implant," Oct. 2, 2001, 6 pages.
Nuvasive, Inc., Corrected Final Invalidity Contentions Regarding U.S. Pat. No. 5,860,973, U.S. Pat. No. 6,592,586 and U.S. Pat. No. 6,945,933 filed in the United States District Court, Southern District of California on Jun. 14, 2010 (and 23 appendices).
Petition for Inter Partes Review of U.S. Pat. No. 8,187,334 Pursuant to 35 U.S.C. 311-319, 37 C.F.R. 42, dated Aug. 14, 2013, 64 pages.
Petition for Inter Partes Review of U.S. Pat. No. 8,361,156 Pursuant to 35 U.S.C. 311-319, 37 C.F.R. 42, dated Aug. 14, 2013, 64 pages.
Second Petition for Inter Partes Review of U.S. Pat. No. 8,187,334 Pursuant to 35 U.S.C. 311-319, 37 C.F.R. 42, dated Aug. 14, 2013, 64 pages.
Second Petition for Inter Partes Review of U.S. Pat. No. 8,361,156 Pursuant to 35 U.S.C. 311-319, 37 C.F.R. 42, dated Aug. 14, 2013, 64 pages.
Stein, et al., "Percutaneous facet joint fusion: Preliminary experience", *Journal of Vascular and Interventional Radiology*, 4:69-74 (1993).
Synthes Vertebral Spacer-PR Brochure, *Synthes Spine*, 2002, 2 pages.
Synthesis Spine Vertebral Spacer-PR Implant, Jun. 2002, 2 pages.
Synthesis Spine Vertebral Spacer-TR Implant, Aug. 2002, 2 pages.
Telamon Implantation Guide, *Medtronic Sofamor Danek*, 2003, 10 pages.
Telamon Verte-Stack PEEK Certebral Body Spacer Brochure, *Medtronic Sofamor Danek*, 2003, 2 pages.
Vamvanij, et al., "Surgical treatment of internal disc disruption: An outcome study of four fusion techniques", *Journal of Spinal Disorders*, 11(5):375-382 (1998).
Zhou et al., Geometrical dimensions of the lower lumbar vertebrae-analysis of data from digitised CT images, *Eur Spine J*, 2000, 9: 242-248.
Final Written Decision in *Medtronic, Inc. v. NuVasive, Inc.*, Case IPR2013-00507, dated Feb. 11, 2015, 14 pages.
Final Written Decision in *Medtronic, Inc. v. NuVasive, Inc.*, Case IPR2013-00508, dated Feb. 11, 2015, 19 pages.
Patent Owner NuVasive Inc.'s Preliminary Response in IPR2013-00504, dated Nov. 25, 2013, 40 pages.
Decision denying Institution of *Inter Partes* review in IPR2013-00504, dated Feb. 13, 2014, 9 pages.
Patent Owner NuVasive Inc.'s Preliminary Response in IPR2013-00506, dated Nov. 25, 2013, 38 pages.
Decision denying Institution of *Inter Partes* review in IPR2013-00506, dated Feb. 13, 2014, 21 pages.
NuVasive Inc's Patent Owner Response in IPR2013-00506, dated May 21, 2014, 66 pages.
Declaration of Dr. Hansen A. Yuan from IPR2013-00506, dated May 21, 2014, 63 pages.
Synthes SVS-PR Guide, *Synthes Spine*, 2002, 8 pages.

(56) References Cited

OTHER PUBLICATIONS

Medtronic Sofamor Danek Boomerang brochure, *Medtronic Sofamor Danek*, 2003, 6 pages.
Synthes Vertebral Spacer—AR brochure, *Synthesis Spine*, 2006, 4 pages.
Saber Surgical Technique /Product Catalogue, *DePuy Spine*, 2004, 12 pages.
Petition for Inter Partes Review of U.S. Pat. No. 8,361,156 Pursuant to 35 U.S.C. 311-319, 37 C.F.R. 42, dated Mar. 5, 2014, 64 pages.
Patent Owner NuVasive Inc.'s Preliminary Response in IPR2013-00507, dated Nov. 25, 2013, 29 pages.
Decision denying Institution of *Inter Partes* review in IPR2013-00507, dated Feb. 13, 2014, 15 pages.
NuVasive Inc's Patent Owner Response in IPR2013-00507, dated May 21, 2014, 50 pages.
Declaration of Dr. Hansen A. Yuan from IPR2013-00507, dated May 21, 2014, 85 pages.
Patent Owner NuVasive Inc.'s Preliminary Response in IPR2013-00508, dated Nov. 25, 2013, 38 pages.
Decision denying Institution of *Inter Partes* review in IPR2013-00508, dated Feb. 13, 2014, 14 pages.
NuVasive Inc's Patent Owner Response in IPR2013-00508, dated May 21, 2014, 66 pages.
Declaration of Dr. Hansen A. Yuan from IPR2013-00508, dated May 21, 2014, 85 pages.

SYSTEM AND METHODS FOR SPINAL FUSION

CROSS-REFERENCE TO RELATED APPLICATIONS

This document is a continuation of U.S. patent application Ser. No. 12/044,917, filed on Mar. 7, 2008 (now U.S. Pat. No. 8,673,005), which claims the benefit of priority from U.S. Provisional Patent Application Ser. No. 60/905,674, entitled "Systems and Methods for Spinal Fusion," and filed on Mar. 7, 2007, the entire contents of these prior application being hereby expressly incorporated by reference into this disclosure as if set forth in its entirety herein.

BACKGROUND OF THE INVENTION

I. Field of the Invention

The present invention relates generally to spinal surgery and, more particularly, to a system and method for spinal fusion comprising a spinal fusion implant of non-bone construction releasably coupled to an insertion instrument dimensioned to introduce the spinal fusion implant into the thoracic region of the spine.

II. Discussion of the Prior Art

Currently there are nearly 500,000 spine lumbar, thoracic and cervical fusion procedures performed each year in the United States. Such procedures are commonly performed to correct problems, such as chronic back or neck pain, which result from degenerated intervertebral discs or trauma. Generally, spinal fusion procedures involve removing some or the entire diseased or damaged disc, and inserting one or more intervertebral implants into the resulting disc space. Introducing the intervertebral implant serves to restore the height between adjacent vertebrae ("disc height"), which reduces if not eliminates neural impingement commonly associated with a damaged or diseased disc.

Autologous bone grafts are widely used as intervertebral implant for thoracic fusion. Autologous bone grafts are obtained by harvesting a section of bone from the iliac crest of the patient and thereafter implanting the article of autologous bone graft to effect fusion. While generally effective, the use of autologous bone grafts suffers certain drawbacks. A primary drawback is the morbidity associated with harvesting the autologous graft from the patient's iliac crest. Another related drawback is the added surgical time required to perform the bone-harvesting.

Allograft bone grafts have been employed with increased regularity in an effort to overcome the drawbacks of autologous bone grafts. Allograft bone grafts are harvested from cadaveric specimens, machined, and sterilized for implantation. While allograft bone grafts eliminate the morbidity associated with iliac crest bone harvesting, as well as decrease the overall surgical time, they still suffer certain drawbacks. A primary drawback is supply constraint, in that the tissue banks that process and produce allograft bone implants find it difficult to forecast allograft given the inherent challenges in forecasting the receipt of cadavers. Another related drawback is that it is difficult to manufacture the allograft with consistent shape and strength characteristics given the variation from cadaver to cadaver.

The present invention is directed at overcoming, or at least improving upon, the disadvantages of the prior art.

SUMMARY OF THE INVENTION

The present invention overcomes the drawbacks of the prior art by providing a spinal fusion system and related methods involving the use of a spinal fusion implant of non-bone construction. The non-bone construction of the spinal fusion implant of the present invention overcomes the drawbacks of the prior art in that it is not supply limited (as with allograft) and does not require harvesting bone from the patient (as with autograft). The spinal fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal or any combination of these materials.

The spinal fusion implant of the present invention may be provided in any number of suitable shapes and sizes depending upon the particular surgical procedure or need. The spinal fusion implant of the present invention may be dimensioned for use in the cervical and/or lumbar spine without departing from the scope of the present invention. For thoracic fusion, the spinal fusion implant of the present invention may be dimensioned, by way of example only, having a width ranging between 15 and 20 mm, a height ranging between 6 and 16 mm, and a length ranging between 20 and 45 mm.

The spinal fusion implant has a top surface, a bottom surface, an anterior side, a posterior side, a proximal side, and a distal side. The spinal fusion implant of the present invention may be provided in such a shape as to promote the proper kyphotic curvature of the spine. Such shape may be accomplished by varying the angle between the top and bottom contact surfaces of the spinal fusion implant to reflect the desired curvature for the vertebral bodies being fused. The desired angle between said top and bottom surfaces may be accomplished by providing the anterior face of the implant with a greater height than the posterior face of the implant. Thus the top and bottom contact surfaces may not be parallel to one another, but rather they may be angled towards one another at the posterior end and angled away from one another at the anterior end.

The spinal fusion implant of the present invention may be provided with any number of additional features for promoting fusion, such as an aperture extending between the upper and lower vertebral bodies which allow a boney bridge to form through the spinal fusion implant of the present invention. Such fusion-promoting aperture may be dimensioned to receive any number of suitable osteoinductive agents, including but not limited to bone morphogenic protein (BMP) and bio-resorbable polymers, including but not limited to any of a variety of poly (D,L-lactide-co-glycolide) based polymers. The spinal fusion implant of the present invention is preferably equipped with one or more lateral openings which aid in visualization at the time of implantation and at subsequent clinical evaluations.

The spinal fusion implant of the present invention may be provided with any number of suitable anti-migration features to prevent the spinal fusion implant from migrating or moving from the disc space after implantation. Suitable anti-migration features may include, but are not necessarily limited to, angled teeth formed along the upper and/or lower surfaces of the spinal fusion implant and/or spike elements disposed partially within and partially outside the top and/or bottom surfaces of the spinal fusion implant. Such anti-migration features provide the additional benefit of increasing the overall surface area between the spinal fusion implant of the present invention and the adjacent vertebrae, which promotes overall bone fusion rates.

The spinal fusion implant of the present invention may be provided with any number of features for enhancing the visualization of the implant during and/or after implantation into a spinal target site. According to one aspect of the present invention, such visualization enhancement features may take the form of the spike elements used for anti-migration, which may be manufactured from any of a variety of suitable materials, including but not limited to a metal, ceramic, and/or polymer material, preferably having radiopaque characteristics. The spike elements may also take any of a variety of suitable shapes, including but not limited to a generally elongated element disposed within the implant such that the ends thereof extend generally perpendicularly from the top and/or bottom surfaces of the implant. The spike elements may each comprise a unitary element extending through upper and lower surfaces or, alternatively, each spike element may comprise a shorter element which only extends through a single surface (that is, does not extend through the entire height of the implant). In any event, when the spike elements are provided having radiodense characteristics and the implant is manufactured from a radiolucent material (such as, by way of example only, PEEK and/or PEKK), the spike elements will be readily observable under X-ray or fluoroscopy such that a surgeon may track the progress of the implant during implantation and/or the placement of the implant after implantation.

The spinal implant of the present invention may be introduced into a spinal target site through the use of any of a variety of suitable instruments having the capability to releasably engage the spinal implant. In a preferred embodiment, the insertion instrument permits quick, direct, accurate placement of the spinal implant of the present invention into the intervertebral space. According to one embodiment, the insertion instrument includes a threaded engagement element dimensioned to threadably engage into a receiving aperture formed in the spinal fusion implant of the present invention.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 2-4 is a perspective view of the thoracic fusion implant of FIG. 1, illustrating (among other things), a fusion aperture extending between top and bottom surfaces, a plurality of visualization apertures extending through the side walls, and a variety of anti-migration features, according to one embodiment of the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The fusion implant system disclosed herein boasts a variety of inventive features and components that warrant patent protection, both individually and in combination.

Figure 1:
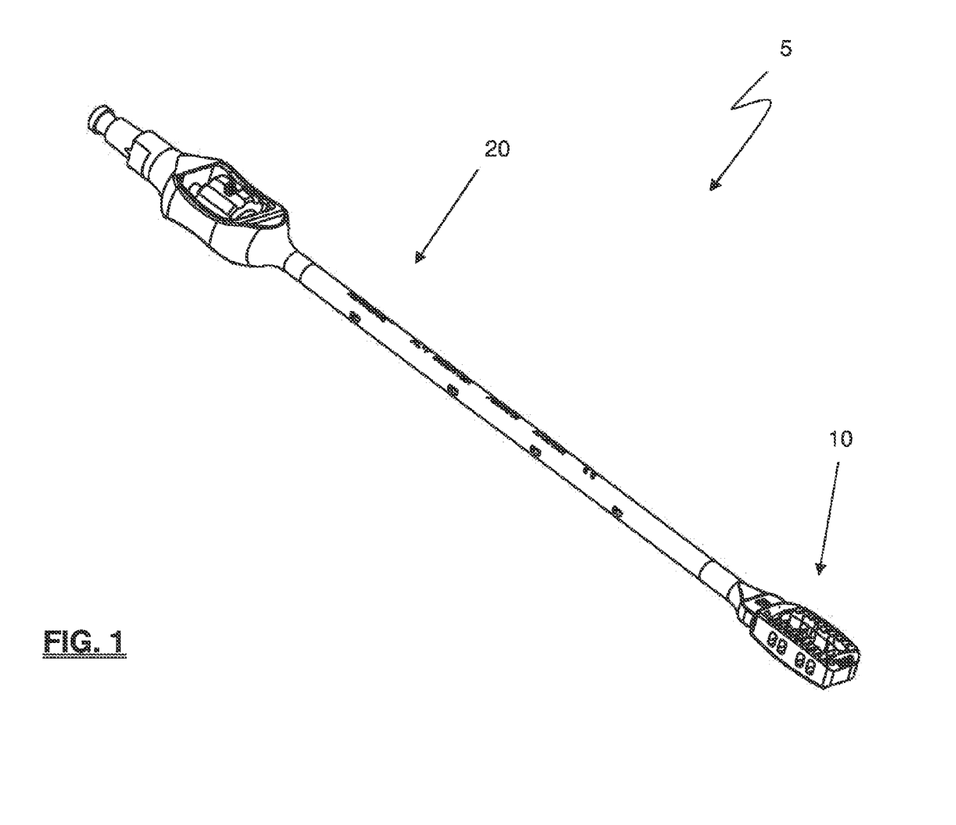
FIG. 1 is a perspective view of a spinal fusion system of the present invention, including a thoracic fusion implant releasably coupled to an insertion instrument, according to one embodiment of the present invention.
Figure 2:
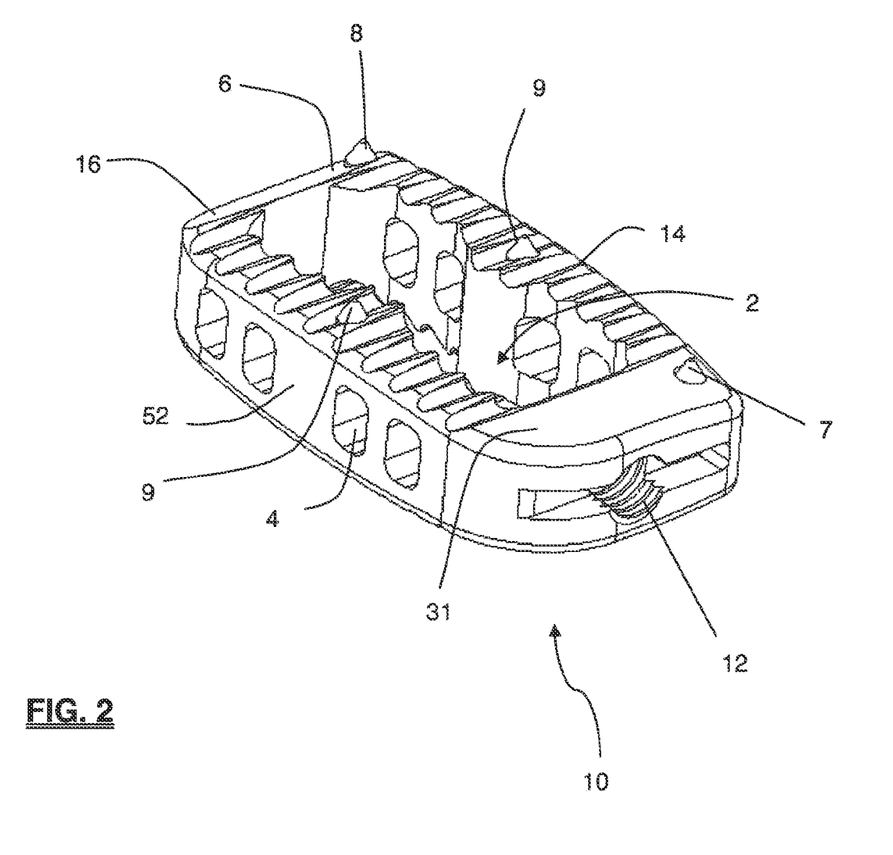
Figure 3:
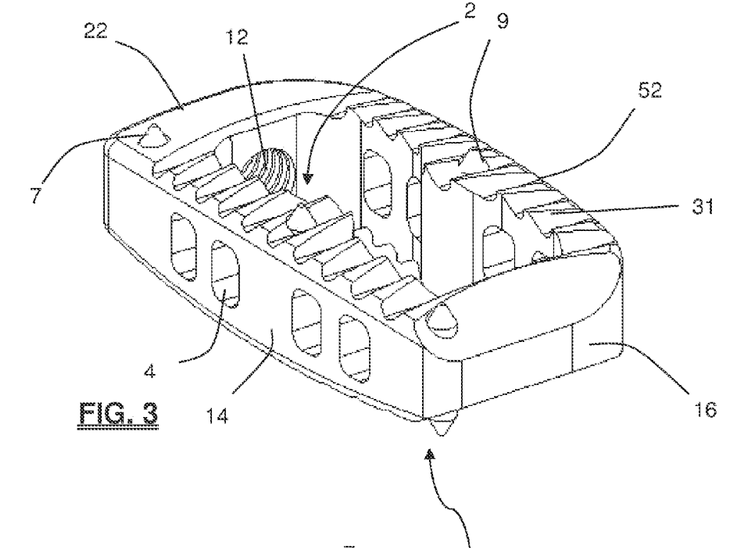
Figure 4:
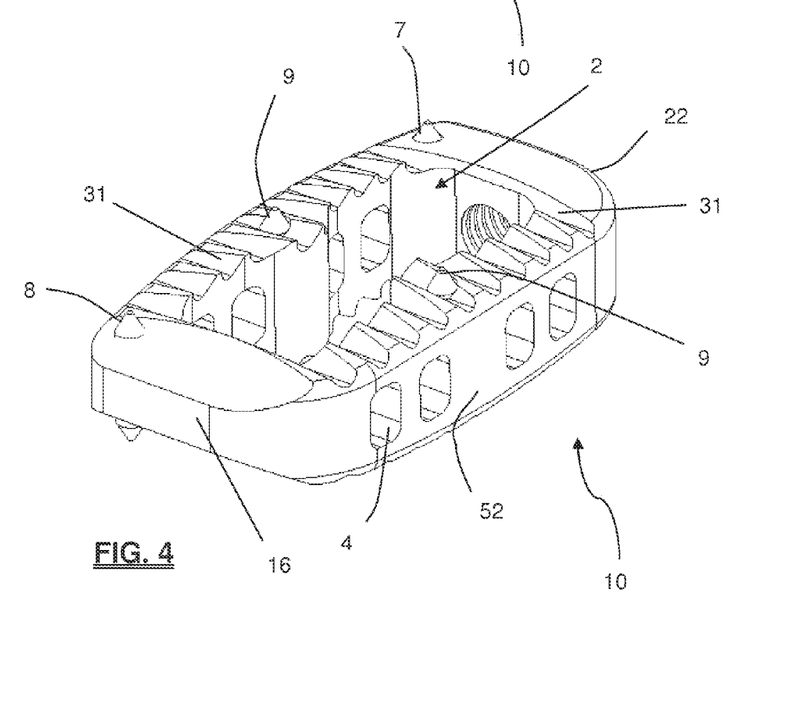
Figure 5:
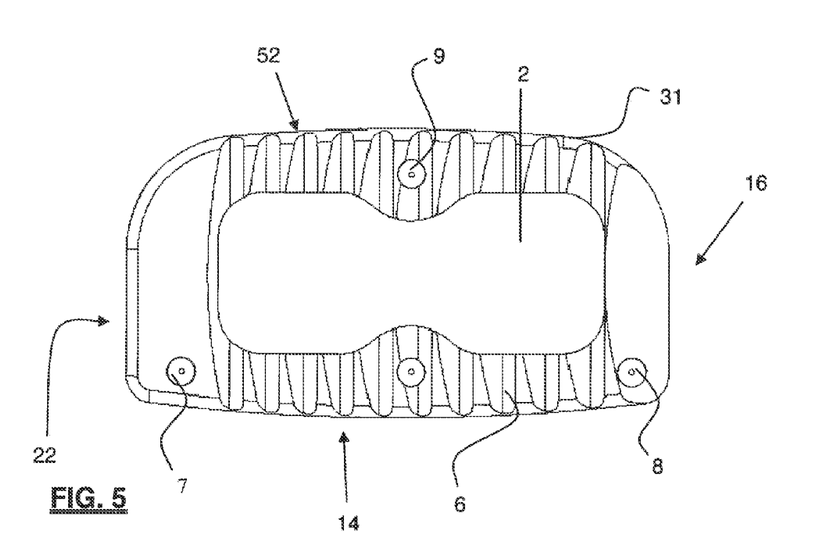
FIG. 5 is a top view of the thoracic fusion implant of FIG. 1, illustrating (among other things) the fusion aperture and the anti-migration features, according to one embodiment of the present invention.
Figure 6:
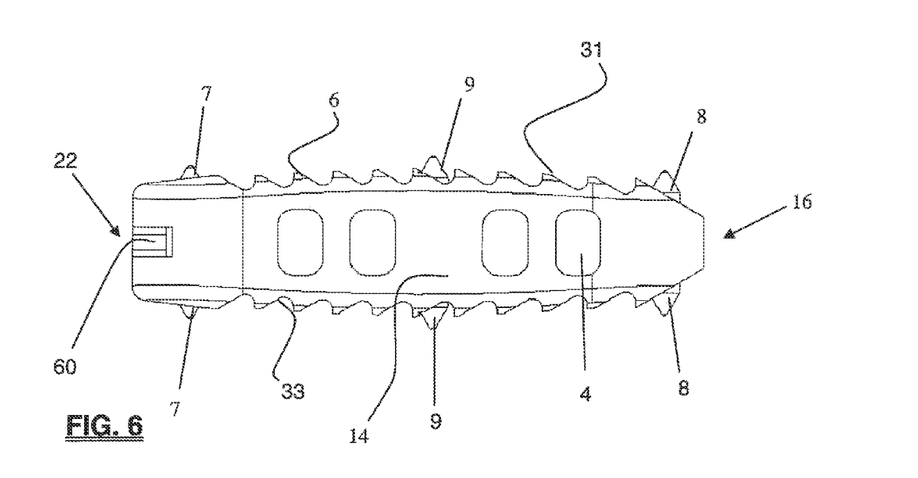
FIG. 6 is a side view of the thoracic fusion implant of FIG. 1, illustrating (among other things) the visualization aperture, the anti-migration features, and a receiving aperture for releasably engaging the insertion instrument of FIG. 1, according to one embodiment of the present invention.
Figure 7:
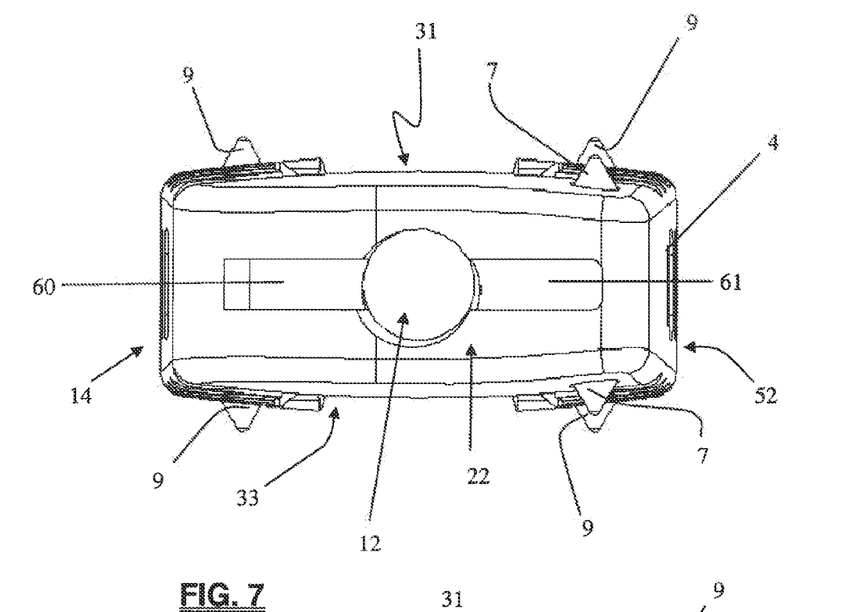
FIG. 7 is an end view of the thoracic fusion implant of FIG. 1, illustrating (among other things) the receiving aperture formed in the proximal end and the anti-migration features, according to one embodiment of the present invention.
Figure 8:
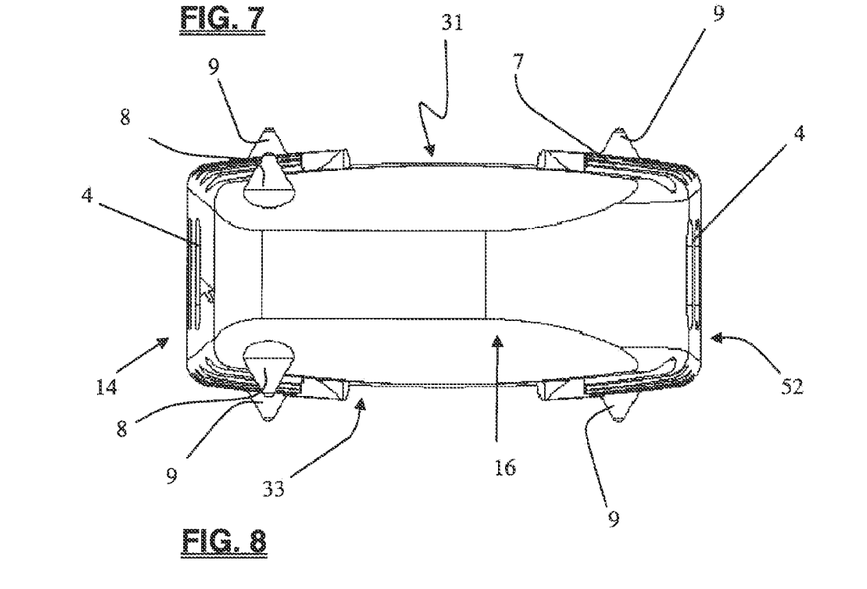
FIG. 8 is an end view of the thoracic fusion implant of FIG. 1, illustrating the distal end and the anti-migration features, according to one embodiment of the present invention.

FIG. 1 illustrates, by way of example only, a spinal fusion system 5 for performing spinal fusion between adjacent thoracic vertebrae, including an exemplary spinal fusion implant 10 and an exemplary insertion instrument 20 provided in accordance with the present invention. The spinal fusion implant 10 may be comprised of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. The spinal fusion implant 10 of the present invention may be dimensioned, by way of example only, having a width ranging between 15 and 20 mm, a height ranging between 6 and 16 mm, and a length ranging between 20 and 45 mm.

As will be described in detail below, the insertion instrument 20 is configured to releasably maintain the exemplary spinal fusion implant 10 in the proper orientation during insertion into a thoracic disc space and thereafter release to deposit the implant 10. The exemplary spinal fusion implant 10, having been deposited in the disc space, facilitates spinal fusion restoring and maintaining a desired disc height as natural bone growth occurs through and/or past the implant 10, resulting in the formation of a boney bridge extending between the adjacent vertebral bodies. The implant 10 is particularly suited for introduction into the disc space via a lateral (trans-psoas) approach to the spine, but may be introduced in any of a variety of approaches, such as posterior, anterior, antero-lateral, and postero-lateral, without departing from the scope of the present invention (depending upon the sizing of the implant 10).

FIGS. 2-8 depict an example embodiment of the spinal fusion implant 10. The spinal fusion implant 10 has a top surface 31, a bottom surface 33, an anterior side 52, a posterior side 14, a proximal side 22, and a distal side 16. The generally D-shaped circumference of implant 10, shown by way of example only, is configured for placement in the thoracic spine. Preferably the anterior side 52 is dimensioned with a length than that of the posterior side 14. This may be accomplished, by way of example, by providing a large radius of curvature of the corners between the anterior side 52 and the distal and proximal ends 16 and 22, by angling the distal and proximal ends 16 and 22 such that they converge towards each other proximate the anterior side 52, or a combination of both. By way of example only the radius of the corners proximate the anterior side 52 may be approximately 0.25 inch (¼ inch) while the radius of the corners proximate the posterior side 14 may be approximately 0.06 inch (1/16 inch). Optionally, to promote the natural kyphotic curvature of the thoracic region of the spine, the posterior side 14 may be dimensioned at a height greater than that of the anterior side 52. This dimensioning allows for the upper 31 and lower surfaces 33 to converge toward one another at the anterior end, thereby forcing the fusing vertebrae to conform to the proper kyphotic curvature. The kyphotic curvature requirements may vary by patient, but the implant angle will likely lie in the range between 1° and 20°, with one example embodiment having and angle of 10°. In one embodiment, the top and bottom surfaces 31, 33 are generally flat across. However, it can be appreciated by one skilled in the art that the top and bottom surfaces 31, 33 may be provided in any number of suitable shapes, including but not limited to concave and/or convex. When provided as convex shapes, the top and bottom surfaces 31, 33 may better match the natural contours of the vertebral end plates.

The exemplary spinal fusion implant 10 also preferably includes anti-migration features designed to increase the friction between the spinal fusion implant 10 and the adjacent contacting surfaces of the vertebral bodies so as to prohibit migration of the spinal fusion implant 10 after implantation. Such anti-migration features may include ridges 6 provided along the top surface 31 and/or bottom surface 33. Additional anti-migration features may also include a spike element 7 disposed within the proximal region of the implant 10, a spike element 8 disposed within the distal region of the implant 10, and a pair of spike elements 9 disposed within the central region of the implant 10, one on the posterior side 14 and one on the anterior side 52. Thus, in a preferred embodiment, posterior side 14 is imbued with 3 spike elements 7, 8, 9, situated one at each end and the center, while the anterior side 52 is situated with a single spike element, situated near the center. This triangular arrangement of spike elements 7, 8, 9, is adopted for placement in the thoracic spine where the anterior portion of the vertebral body narrows sharply and is in clear proximity to the great vessels. Spike elements 7, 8, 9 may extend from the top surface 31 and/or bottom surface 33 within the respective proximal, distal and central regions of the implant 10. The spike elements 7, 8, 9 may be manufactured from any of a variety of suitable materials, including but not limited to a metal, ceramic, and/or polymer material, preferably having radiopaque characteristics. The spike elements 7, 8, 9 may also take any of a variety of suitable shapes, including but not limited to a generally elongated element disposed within the implant 10 such that the ends thereof extend generally perpendicularly from the upper and/or lower surfaces 31, 33 of the implant 10. As best appreciated in FIGS. 6-8, the spike elements 7, 8, 9 may each comprise a unitary element extending through top and bottom surfaces 31, 33. Alternatively, each spike element 7, 8, 9 may comprise a shorter element which only extends through a single surface 31, 33 (that is, does not extend through the entire height of the implant 10). In any event, when the spike elements 7, 8, 9 are provided having radiodense characteristics and the implant 10 is manufactured from a radiolucent material (such as, by way of example only, PEEK and/or PEKK), the spike elements 7, 8, 9 will be readily observable under X-ray or fluoroscopy such that a surgeon may track the progress of the implant 10 during implantation and/or the placement of the implant 10 after implantation.

The spinal fusion implant 10 of the present invention may be provided with any number of additional features for promoting fusion, such as an aperture 2 extending between the upper and lower vertebral bodies which allow a boney bridge to form through the spinal fusion implant 10. According to a still further aspect of the present invention, this fusion may be facilitated or augmented by introducing or positioning various osteoinductive materials within aperture 2 and/or adjacent to the spinal fusion implant 10. Such osteoinductive materials may be introduced before, during, or after the insertion of the exemplary spinal fusion implant 10, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including but not limited to any of a variety of poly (D,L-lactide-co-glycolide) based polymers. The large fusion aperture 2 of the implant 10 may be provided in any of a variety of suitable shapes, including but not limited to the generally hourglass shape best viewed in FIG. 5, or a generally, rectangular, circular, oblong and/or triangular shape or any combination thereof. The preferred hourglass shape, shown in FIG. 5, maximizes the open area for boney growth through the implant 10 while still providing added support and contact surface area along the ends and enter of the implant.

The spinal fusion implant 10 of the present invention is preferably equipped with one or more visualization apertures 4 situated along the anterior 14 and posterior 52 sides, which aid in visualization at the time of implantation and at subsequent clinical evaluations. The plurality of visualization apertures 4 will allow a clinician to make visual observations of the degree of bony fusion un-obscured by the anterior 14 or posterior sides 52. Specifically, based on the generally radiolucent nature of the implant 10, the visualization apertures 4 provide the ability to visualize the interior of the implant 10 during X-ray and/or other suitable imaging techniques which are undertaken from the side (or "lateral") perspective of the implant 10 (e.g. images taken from anterior/posterior position where the implant is inserted in a preferred position from a lateral approach). If fusion has taken place, the visualization apertures 4 will provide a method for the surgeon to make follow up assessments as to the degree of fusion without any visual interference from the spinal fusion implant 10. Further, the visualization apertures 4 will provide an avenue for cellular migration to the exterior of the spinal fusion implant 10. Thus, the spinal fusion implant 10 will serve as additional scaffolding for bone fusion on the exterior of the spinal fusion implant 10. The visualization apertures 4 may be provided in any of a variety of suitable shapes, including but not limited to the generally oblong shape best viewed in FIG. 6, or a generally circular, rectangular and/or triangular shape or any combination thereof.

The spinal fusion implant 10 may be provided with any number of suitable features for engaging the insertion instrument 20 without departing from the scope of the present invention. As best viewed in FIG. 7, one engagement mechanism involves providing a threaded receiving aperture 12 in the proximal sidewall 22 of the spinal fusion implant 10 of the present invention. The threaded receiving aperture 12 is dimensioned to threadably receive a threaded connector 24 on the insertion instrument 20 (as will be described in greater detail below). The receiving aperture 12 extends inwardly from the proximal side 22 in a generally perpendicular fashion relative to the proximal side 22. Although shown as having a generally circular cross-section, it will be appreciated that the receiving aperture 12 may be provided having any number of suitable shapes or cross-sections, including but not limited to rectangular or triangular. In addition to the receiving aperture 12, the spinal fusion implant 10 is preferably equipped with a pair of grooved purchase regions 60, 61 extending generally horizontally from either side of the receiving aperture 12. The grooved purchase regions 60, 61 are dimensioned to receive corresponding distal head ridges 62, 63 on the insertion instrument 20 (as will be described in greater detail below), which collectively provide an enhanced engagement between the implant 10 and the insertion instrument 20.

Figure 9:
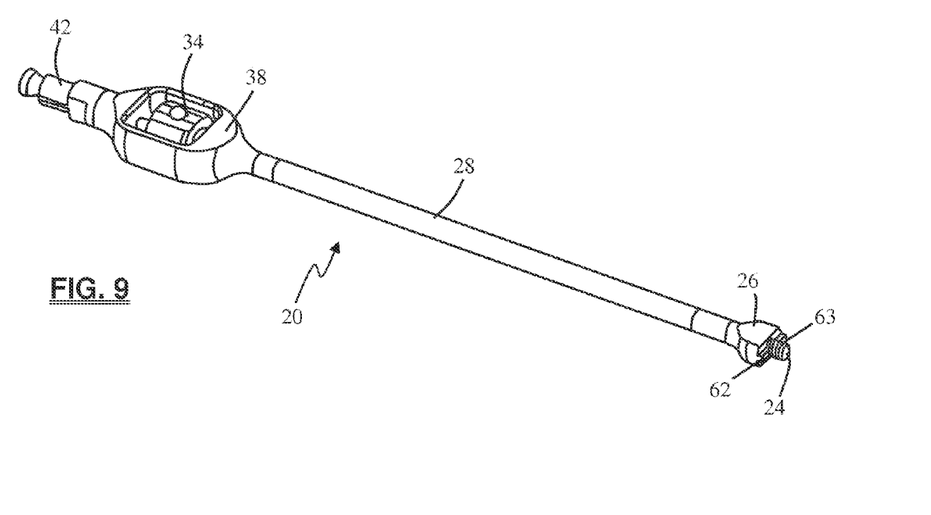
FIG. 9 is a perspective view of the insertion instrument of FIG. 1 in a fully assembled form, according to one embodiment of the present invention.
Figure 10:
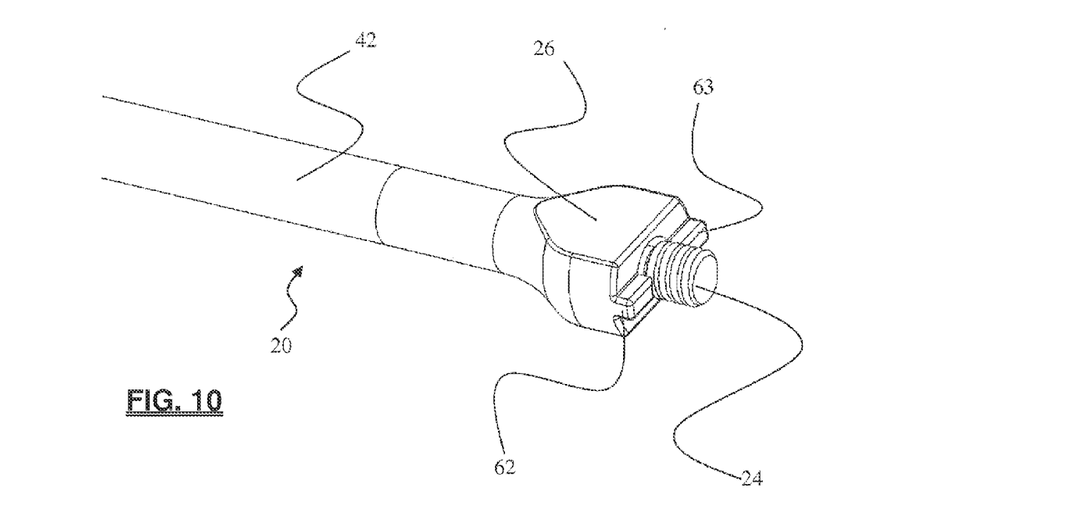
FIG. 10 is an enlarged perspective view of the distal region of the insertion instrument of FIG. 1, according to one embodiment of the present invention.
Figure 11:
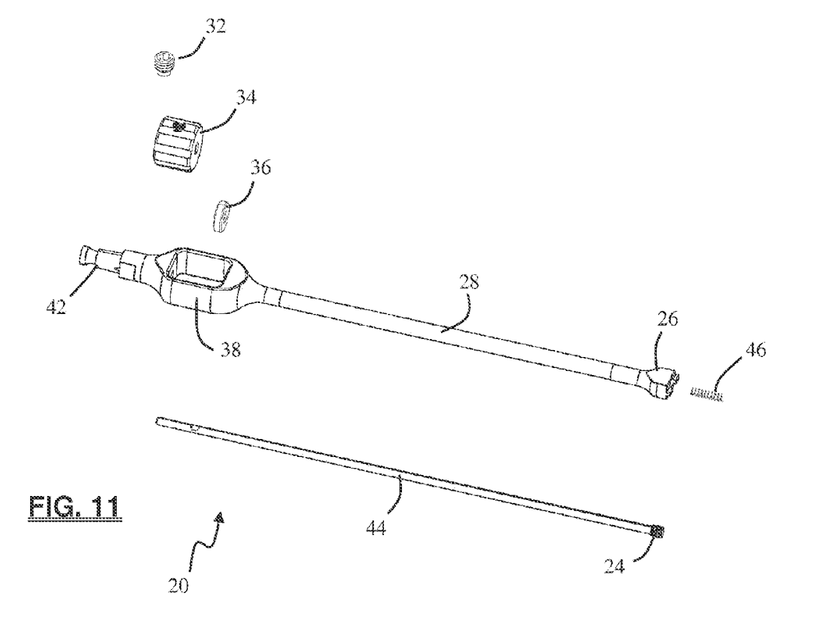
FIG. 11 is a perspective exploded view of the insertion instrument of FIG. 1, illustrating the component parts of the insertion instrument according to one embodiment of the present invention.

FIGS. 9-11 detail the exemplary insertion instrument 20 according to one embodiment of the invention. The exemplary insertion instrument 20 includes an elongated tubular element 28 and an inserter shaft 44. The elongated tubular element 28 is constructed with a distal head 26 at its distal end, distal head ridges 62, 63 on the distal end of the distal head 26, a thumbwheel housing 38 at its proximal end and a handle 42 at its proximal end. The elongated tubular element 28 is generally cylindrical and of a length sufficient to allow the device to span from the surgical target site to a location sufficiently outside the patient's body so the handle 42 and the thumbwheel housing 38 can be easily accessed by a clinician or a complimentary controlling device.

The elongated tubular element 28 is dimensioned to receive a spring 46 and the proximal end of the inserter shaft 44 into the inner bore 64 of the elongated tubular element 28. The inserter shaft 44 is dimensioned such that the threaded connector 24 at the distal end of the inserter shaft 44 just protrudes past the distal head ridges 62, 63 to allow engagement with the receiving aperture 12 of the spinal fusion implant 10. It should be appreciated by one skilled in the art that such a construction allows the inserter shaft 44 to be able to rotate freely within the elongated tubular element 28 while stabilized by the spring 46 to reduce any slidable play in the insertion instrument 20.

The handle 42 is generally disposed at the proximal end of the insertion instrument 20. The handle 42 is fixed to the thumbwheel housing 38 allowing easy handling by the clinician. Because the handle 42 is fixed the clinician has easy access to the thumbwheel 34 and can stably turn the thumbwheel 34 relative to the thumbwheel housing 38. Additionally, the relative orientation of the thumbwheel housing 38 to the handle 42 orients the clinician with respect to the distal head 26 and distal head ridge 62. By way of example, the thumbwheel housing 38 holds a thumbwheel 34, a set screw 32, and a spacer 36. The inserter shaft 44 is attached to the thumbwheel 34 and is freely rotatable with low friction due to the spacer 36. One skilled in the art can appreciate myriad methods of assembling a housing similar to the above described.

The distal head ridges 62, 63 are dimensioned to fit slidably into the purchase regions 60, 61 with low friction to allow accurate engagement of the threaded connector 24 to the receiving aperture 12 of the spinal fusion implant 10. In the presented embodiment, the outer dimension of the threaded connector 24 is smaller than the largest outer dimension of the distal head 26 and elongated tubular element 28. Alternatively, other methods of creating a gripping surface are contemplated including but not limited to knurling or facets.

In order to use the system to perform a spinal fusion procedure, the clinician must first designate the appropriate implant size (and optionally, angulation). After the spinal fusion implant 10 is chosen, the distal head ridges 62, 63 of the inserter shaft 44 are inserted into the purchase regions 60, 61 of the spinal fusion implant 10. At that time the spinal fusion implant 10 and insertion instrument 20 are slidably engaged with one another. Before the clinician can manipulate the combined spinal fusion implant 10 and insertion instrument 20, they must be releasably secured together. In order to secure the spinal fusion implant 10 onto the threaded connector 24 of the inserter instrument 20, the clinician employs the thumbwheel 34 to rotate the inserter shaft 44 and threaded connector 24. The rotation of the threaded connector 24 will releasably engage the receiving aperture 12 of the spinal fusion implant 10 and stabilize the insertion instrument 20 relative to the spinal fusion implant 10.

A clinician can utilize the secured system in either an open or minimally invasive spinal fusion procedure. In either type of procedure, a working channel is created in a patient that reaches the targeted spinal level. After the creation of that channel, the intervertebral space may be prepared via any number of well known preparation tools, including but not limited to kerrisons, rongeurs, pituitaries, and rasps. After preparation, the insertion instrument 20 is used to place a spinal fusion implant 10 into the prepared intervertebral space. Once the implant 10 is inserted into the prepared space, the implant 10 is released from the insertion instrument 20 by rotating the thumbwheel 34 to disengage the threaded connector 24 from the receiving aperture 12. This motion removes the compressive force on the purchase regions 60, 61 between the distal head 26 and the distal head ridges 62, 63 of the spinal fusion implant 10 and allows the insertion instrument to be slidably removed from the implant 10. After the threaded connector 24 is disengaged from the implant 10, the insertion instrument 20 is removed from the working channel and the channel is closed. As previously mentioned, additional materials may be included in the procedure before, during or after the insertion of the spinal fusion implant 10 to aid the natural fusion of the targeted spinal level.

Figure 12:
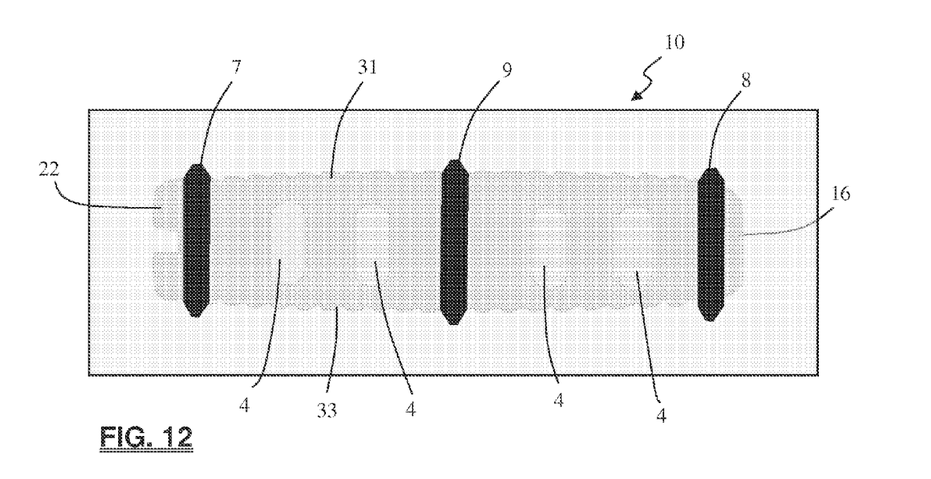
FIG. 12 represents a flourographic image of the implant and is a side view illustrating the "enhanced visualization" feature of the present invention as employed within a thoracic fusion implant according, to one embodiment of the present invention.

The enhanced visualization features of the implant 10 is explained in greater detail with reference to FIG. 12, illustrating the implant 10 dimensioned particularly for use in a lateral approach having (by way of example only) a width ranging between 15 and 20 mm, a height ranging between 6 and 16 mm, and a length ranging between 20 and 45 mm. Furthermore, FIG. 12 illustrates the implant 10 from a side perspective clearly showing the location of the spike elements 7, 8, 9 relative to the implant 10 and the visualization apertures 4.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined by the appended claims.

For example, while described herein primarily with reference to the thoracic spinal surgery, it is to be readily appreciated that the spinal fusion implants of the present invention may be suitable for accomplishing fusion in the cervical or lumbar spine without departing from the scope of the present invention. It should be noted that implants designed for the cervical and lumbar regions may be composed in a similar manner, but having a lordosis-promoting shape, rather than the kyphosis promoting shape described above. Specifically, the anterior side may be dimensioned to have a height greater than the posterior side. Those implants 10 designed to be inserted into the cervical region may be very similar to those to be inserted into the thoracic region, albeit smaller, while those designed for the lumbar region may be larger. Moreover, it is to be readily appreciated that the insertion tools described herein may be employed with implants of any number of suitable constructions, including but not limited to metal, ceramic, plastic or composite.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fusion implant for implantation via a lateral surgical approach in an interbody space between an upper vertebral body and a lower vertebral body, comprising:
    proximal and distal sidewalls, and an anterior sidewall configured to face an anterior aspect of said interbody space when said implant is positioned within the interbody space, and a posterior sidewall configured to face a posterior aspect of said interbody space when said implant is positioned within the interbody space, said distal sidewall, proximal sidewall, anterior sidewall, and posterior sidewall comprising a radiolucent material, wherein the anterior sidewall is curved with respect to and positioned generally opposite to the posterior sidewall, and wherein said distal sidewall, proximal sidewall, anterior sidewall, and posterior sidewall provide a generally D-shaped circumference of said implant;
    wherein the posterior, anterior, proximal, and distal sidewalls define a top surface including anti-migration features along at least the posterior sidewall and the anterior sidewall, wherein the anti-migration features are operable to engage the upper and lower vertebral bodies in a lumbar spine, wherein the top surface includes a smooth top section extending along at least a portion of the distal sidewall to a distal edge of the distal sidewall;
    wherein the posterior, anterior, proximal, and distal sidewalls define a bottom surface including anti-migration features along at least the posterior sidewall and the anterior sidewall, wherein the anti-migration features are operable to engage the upper and lower vertebral bodies in the lumbar spine, wherein the bottom surface includes a smooth bottom section extending along at least a portion of the distal sidewall to the distal edge of the distal sidewall, and wherein the smooth bottom section and the smooth top section taper toward the distal edge of the distal sidewall;
    wherein the posterior, anterior, proximal, and distal sidewalls define a single fusion aperture extending from the top surface to the bottom surface, wherein the single fusion aperture extends from an inner surface of the proximal sidewall to an inner surface of the distal sidewall and extends from an inner surface of the posterior sidewall to an inner surface of the anterior sidewall;
    wherein the spinal fusion implant has a longitudinal length extending between the proximal sidewall and the distal sidewall, a maximum width smaller than the longitudinal length and extending perpendicularly to the longitudinal length and between the posterior sidewall and the anterior sidewall, and a maximum height smaller than the maximum width and extending perpendicularly to the maximum width between the top surface and the bottom surface; and
    at least three radiopaque elongate elements disposed at least partially within said radiolucent material and extending parallel to said height.

2. The spinal fusion implant of claim 1:
    wherein the proximal sidewall connects the anterior sidewall to the posterior sidewall, wherein the proximal sidewall intersects a proximal end of the anterior sidewall at a first junction and intersects a proximal end of the posterior sidewall at a second junction, wherein an outer surface of the first junction has a larger radius of curvature than an outer surface of the second junction; and
    wherein the distal sidewall connects the anterior sidewall to the posterior sidewall, wherein the distal sidewall intersects a distal end of the anterior sidewall at a third junction and intersects a distal end of the posterior sidewall at a fourth junction, wherein an outer surface of the third junction has a greater radius of curvature than an outer radius of the fourth junction.

3. The spinal fusion implant of claim 1, wherein the proximal sidewall defines a threaded receiving aperture extending through the proximal sidewall, wherein the proximal sidewall defines a first groove region extending between the threaded receiving aperture and an outer surface of the anterior sidewall and a second groove region extending between the threaded receiving aperture and an outer surface of the posterior sidewall, and wherein the threaded receiving aperture and the first and second groove regions are configured for releasably mating with a distal connector of an insertion tool.

4. The spinal fusion implant of claim 1, wherein the longitudinal length is 45 mm or larger for laterally inserting the implant between the upper and lower vertebral bodies in the lumbar spine.

5. The spinal fusion implant of claim 1, wherein the anti-migration features comprise a plurality of spike elements.

6. The spinal fusion implant of claim 1, wherein the maximum width of the implant from an outer surface of the posterior sidewall to an outer surface of the anterior sidewall is greater than a width at the distal edge of the distal sidewall and is greater than a trailing end width at a proximal edge of the proximal sidewall.

7. The spinal fusion implant of claim 1, wherein each of the posterior, proximal, and distal sidewalls have at least one surface with at least one portion that is substantially planar and wherein the top and bottom surfaces have an at least partially convex curvature and are contoured to approximate natural contours of lumbar vertebral endplates when inserted laterally between lumbar vertebrae.

8. The spinal fusion implant of claim 1, wherein the spinal fusion implant has a lordosis-promoting shape such that a maximum height of the anterior sidewall is greater than a maximum height of the posterior sidewall.

9. A spinal fusion implant for implantation via a lateral surgical approach in an interbody space between adjacent vertebrae in a spine, comprising:
    a posterior sidewall;
    an anterior sidewall curved with respect to and positioned opposite to the posterior sidewall, wherein the anterior sidewall has a greater length than the posterior sidewall;
    a proximal sidewall connecting the anterior sidewall to the posterior sidewall, wherein the proximal sidewall intersects a proximal end of the anterior sidewall at a first junction and intersects a proximal end of the posterior sidewall at a second junction, wherein an outer surface of the first junction has a larger radius of curvature than an outer surface of the second junction;

a distal sidewall connecting the anterior sidewall to the posterior sidewall, wherein the distal sidewall intersects a distal end of the anterior sidewall at a third junction and intersects a distal end of the posterior sidewall at a fourth junction, wherein an outer surface of the third junction has a greater radius of curvature than an outer radius of the fourth junction;

wherein the posterior, anterior, proximal, and distal sidewalls define a top surface having anti-migration features extending along at least the posterior sidewall and the anterior sidewall, wherein the anti-migration features are configured to hinder migration of the spinal fusion implant after implantation between the adjacent vertebrae in the spine, wherein the top surface includes a smooth top section extending along at least a portion of the distal sidewall to a distal edge of the distal sidewall;

wherein the posterior, anterior, proximal, and distal sidewalls define a bottom surface having anti-migration features along at least the posterior sidewall and the anterior sidewall, wherein the anti-migration features are configured to hinder migration of the spinal fusion implant after implantation between the adjacent vertebrae in the spine, wherein the bottom surface includes a smooth bottom section extending along at least a portion of the distal sidewall to the distal edge of the distal sidewall, and wherein the smooth bottom section and the smooth top section taper toward the distal edge of the distal sidewall;

wherein the spinal fusion implant has a longitudinal length extending between the proximal sidewall and the distal sidewall, a maximum width smaller than the longitudinal length and extending perpendicularly to the longitudinal length and between the posterior sidewall and the anterior sidewall, and a maximum height smaller than the maximum width and extending perpendicularly to the maximum width between the top surface and the bottom surface;

wherein the posterior, anterior, proximal, and distal sidewalls define a single fusion aperture extending through the spinal fusion implant from the top surface to the bottom surface, wherein the single fusion aperture extends from an inner surface of the proximal sidewall to an inner surface of the distal sidewall and extends from an inner surface of the posterior sidewall to an inner surface of the anterior sidewall, and wherein the spinal fusion implant is sized and configured to be implanted between the adjacent vertebrae in the spine via the lateral surgical approach and provides a generally D-shaped outer circumferential shape when viewed from a top of the spinal fusion implant and when viewed from a bottom of the spinal fusion implant.

10. The spinal fusion implant of claim 9, wherein the radius of at least one of the first and third junctions is approximately 0.25 inches and the radius of at least one of the second and fourth junctions is approximately 0.06 inches.

11. The spinal fusion implant of claim 9, wherein the proximal sidewall defines a threaded receiving aperture extending through the proximal sidewall, wherein the proximal sidewall defines a first groove region extending between the threaded receiving aperture and an outer surface of the anterior sidewall and a second groove region extending between the threaded receiving aperture and an outer surface of the posterior sidewall, and wherein the threaded receiving aperture and the first and second groove regions are configured for releasably mating with a distal connector of an insertion tool.

12. The spinal fusion implant of claim 9, wherein the posterior, anterior, proximal, and distal sidewalls comprise radiolucent material, the spinal fusion implant further comprising a plurality of radiopaque elongate elements positioned in the radiolucent material and oriented parallel to the height of the implant.

13. The spinal fusion implant of claim 9, wherein the anti-migration features comprise a plurality of spike elements.

14. The spinal fusion implant of claim 9, wherein the maximum width of the implant from an outer surface of the posterior sidewall to an outer surface of the anterior sidewall is greater than a leading end width at the distal edge of the distal sidewall and is greater than a trailing end width at a proximal edge of the proximal sidewall.

15. The spinal fusion implant of claim 9, wherein each of the posterior, proximal, and distal sidewalls have at least one surface with at least one portion that is substantially planar and wherein the top and bottom surfaces have an at least partially convex curvature and are contoured to approximate natural contours of lumbar vertebral endplates when inserted laterally between lumbar vertebrae.

16. The spinal fusion implant of claim 9, wherein the top and bottom surfaces are contoured to approximate natural contours of lumbar vertebral endplates when inserted laterally between lumbar vertebrae, wherein the spinal fusion implant has a lordosis-promoting shape, and wherein a maximum height of the anterior sidewall is greater than a maximum height of the posterior sidewall.

17. The spinal fusion implant of claim 9, wherein the spinal fusion implant has a width between 15 to 20 mm.

18. A method comprising:
creating a lateral, trans-psoas surgical corridor to a lumbar spine,
inserting a spinal fusion implant through the lateral, trans-psoas surgical corridor to the lumbar spine, wherein the spinal fusion implant includes: a top surface including anti-migration elements for contacting an upper lumbar vertebral body, a bottom surface including anti-migration elements for contacting a lower lumbar vertebral body, proximal and distal walls, a curved anterior wall, and a posterior wall, said distal wall, proximal wall, anterior wall, and posterior wall comprising a radiolucent material, wherein said distal wall, proximal wall, anterior wall, and posterior wall provide a generally D-shaped circumference of said implant; wherein said implant has a longitudinal length extending from a proximal end of said proximal wall to a distal end of said distal wall, a maximum width extending generally perpendicularly relative to the longitudinal length, and a height extending generally perpendicularly relative to the longitudinal length and the maximum width, wherein said longitudinal length is greater than said maximum width and said height; a single fusion aperture extending between said top surface and said bottom surface, wherein said single fusion aperture is positioned between said distal wall, proximal wall, anterior wall, and posterior wall, said single fusion aperture having: a longitudinal aperture length extending generally parallel to the longitudinal length of said implant, and a lateral aperture width extending generally parallel to the maximum width of said implant, wherein the longitudinal aperture length extends for greater than half of the longitudinal length of said implant, and wherein the longitudinal aperture width extends for greater than half of the maximum width of said implant; and at least three radiopaque elongate elements disposed at least partially within said radiolucent material and extending parallel to said height;

introducing the spinal fusion implant laterally into a disc space between adjacent lumbar vertebrae such that the curved anterior wall is positioned toward an anterior aspect of the disc space and that the posterior wall is positioned toward the posterior aspect of the disc space, wherein osteoinductive material is positioned within the single fusion aperture to promote formation of a bony bridge through the single fusion aperture.

19. The method of claim 18, wherein the proximal wall defines a threaded receiving aperture extending through the proximal wall, wherein the proximal wall defines a first groove region extending between the threaded receiving aperture and an outer surface of the anterior wall and a second groove region extending between the threaded receiving aperture and an outer surface of the posterior wall, and wherein the spinal fusion implant is inserted via an insertion tool having a distal connector releasably mated with the threaded receiving aperture and the first and second groove regions.

20. The method of claim 18, wherein a first of said at least three radiopaque elongate elements is disposed at a position distal of the single fusion aperture, a second of said at least three radiopaque elongate elements is disposed at a position proximal of the single fusion aperture, and a third of said at least three radiopaque elongate elements is disposed in the anterior wall at a position to the side of the single fusion aperture.

\* \* \* \* \*